United States Patent [19]

Wang

[11] Patent Number: 4,532,216
[45] Date of Patent: Jul. 30, 1985

[54] USE OF QUATERNARY AMMONIUM POLYELECTROLYTE SALTS IN TEST MEANS, TEST DEVICE AND METHOD FOR DETERMINING THE IONIC STRENGTH OR SPECIFIC GRAVITY OF A LIQUID SAMPLE

[75] Inventor: Joseph Y. Wang, Elkhart, Ind.

[73] Assignee: Miles Laboratories, Inc., Elkhart, Ind.

[21] Appl. No.: 453,874

[22] Filed: Dec. 27, 1982

[51] Int. Cl.$^3$ .................. G01N 9/36; G01N 31/04
[52] U.S. Cl. ........................ 436/2; 73/32 R; 422/56; 422/57; 436/169
[58] Field of Search .................. 436/2, 163, 164, 169; 422/56, 57, 58; 73/32 R; 427/2

[56] References Cited

U.S. PATENT DOCUMENTS 3,449,080  6/1969  Edwards ........................ 422/56 X
4,318,709  3/1982  Falb et al. ..................... 422/57 X
4,376,827  3/1983  Stiso et al. .................... 436/169 X

FOREIGN PATENT DOCUMENTS 2037981  7/1980  United Kingdom ............... 73/32 R

OTHER PUBLICATIONS

Burkhardt et al., Clinical Chemistry, vol. 28, No. 10, pp. 2068–2072, (1982).

Primary Examiner—Barry S. Richman
Assistant Examiner—Robert J. Hill, Jr.
Attorney, Agent, or Firm—Edward H. Gorman, Jr.

[57] ABSTRACT

A test means, test device, and method for determining the ionic strength or specific gravity of a test sample as well as a method for making the device, are disclosed. The test means comprises a weakly acidic polyelectrolyte polymer, at least 50 percent of the carboxyl groups of which are present in the form of the salt of a quaternary ammonium ion having the structure

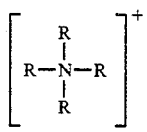

in which the R substituents, same or different, are hydrogen, lower alkyl or aryl, with the proviso that at least one of R is other than hydrogen; and an indicator means capable of producing a detectable response to ion exchange between the polyelectrolyte salt and the test sample. The device comprises a carrier matrix incorporated with the test means. The method for determining the ionic strength or specific gravity comprises contacting the test sample with the test means or device and observing a detectable response. The method for making the device comprises the steps of reacting the weakly acidic polyelectrolyte polymer with sufficient quaternary ammonium hydroxide to neutralize at least 50 percent of the carboxyl groups to form a polyelectrolyte salt, and incorporating the salt and a pH indicator with a carrier matrix.

35 Claims, 2 Drawing Figures

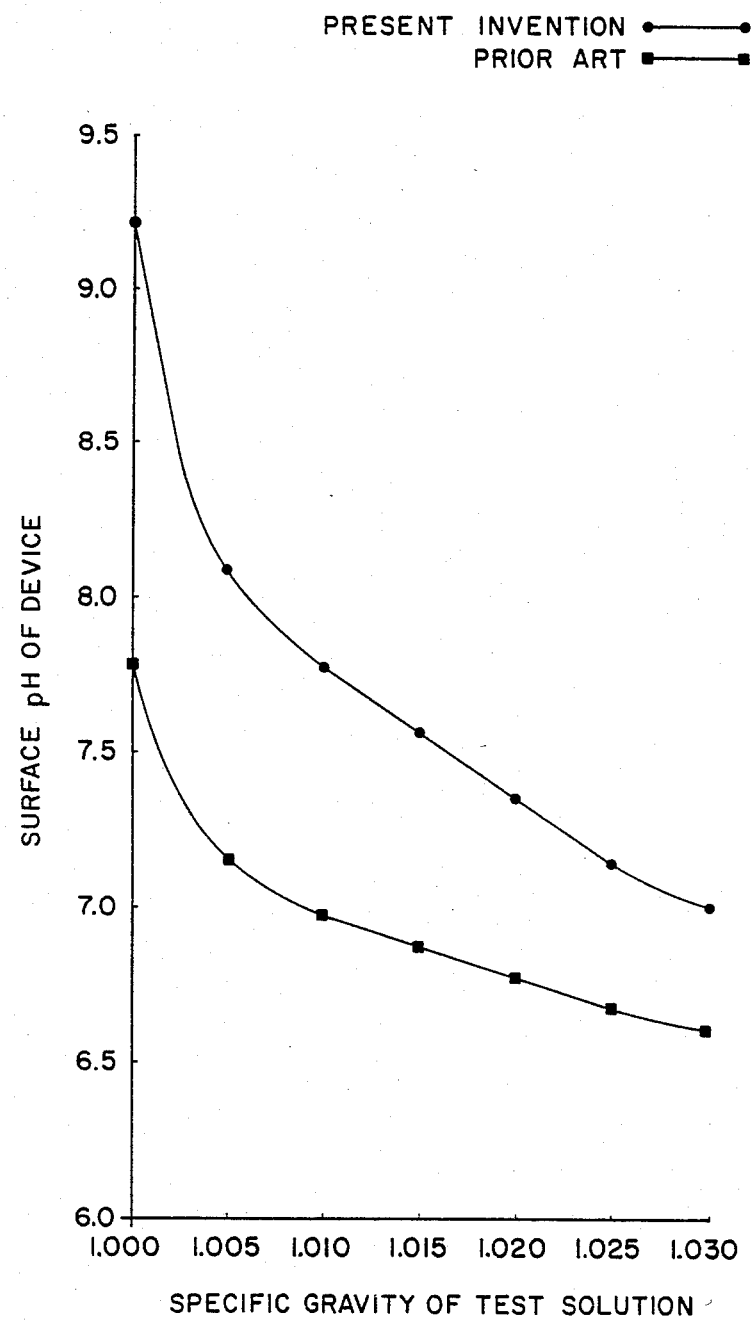
FIG. I

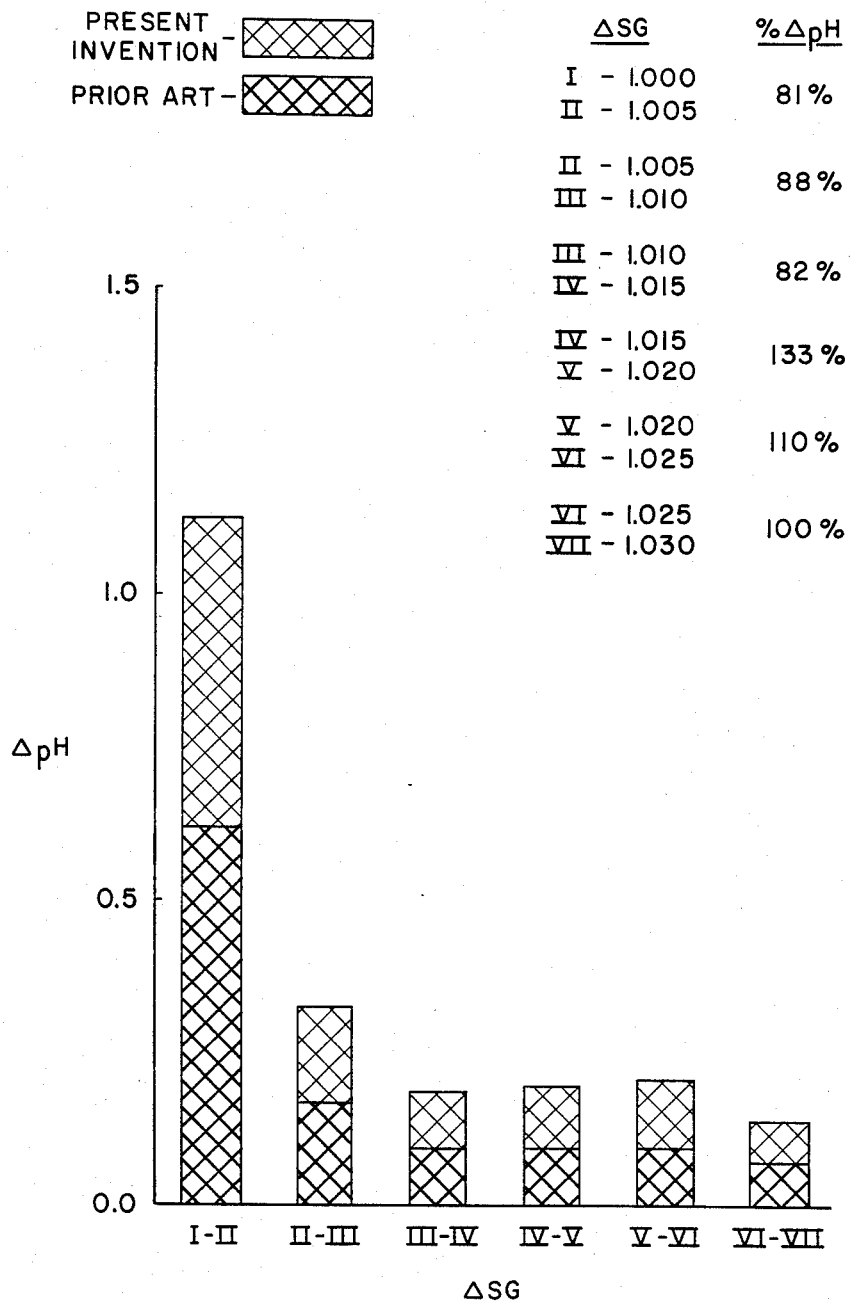
FIG. II

USE OF QUATERNARY AMMONIUM POLYELECTROLYTE SALTS IN TEST MEANS, TEST DEVICE AND METHOD FOR DETERMINING THE IONIC STRENGTH OR SPECIFIC GRAVITY OF A LIQUID SAMPLE

CONTENTS

1. Introduction
    1.1 Applications of the Invention
    1.2 Relationship Between Specific Gravity and Ionic Strength
2. Background of the Invention
3. Summary of the Invention
4. Brief Description of the Drawings
5. Definitions
6. Polyelectrolytes and Their Salts
    6.1 Weakly Acidic Polyelectrolytes
    6.2 Quaternary Ammonium Ions
    6.3 Preparation of the Polyelectrolyte Salt
7. pH Indicator Means
8. The Test Device
    8.1 The Carrier Matrix
    8.2 Incorporation of the Matrix with the Composition
    8.3 Preparation of a Dip-and-Read Device
9. Reference Standard
10. Examples
    10.1 Preparation of the Polyelectrolyte Salt
    10.2 Preparation of Test Devices
    10.3 Evaluation of the Test Device

1. INTRODUCTION

The present invention relates to the determination of the ionic strength or specific gravity of a test sample. A test means, test device and method are disclosed for making this determination in an aqueous test sample. These aspects of the invention provide a simple, facile method for analyzing ionic strength or specific gravity whereby results are available to the assayist momentarily after merely contacting a test sample solution with the test means or device. There is no need for such cumbersome apparatuses and procedures as hydrometers, urinometers, gravimeters, calibration, the cleaning of equipment, or other trappings of prior procedures.

1.1 Applications of the Invention

The determination of the specific gravity of a liquid has application in numerous arts. Such seemingly unrelated disciplines as brewing, urinalysis, water purification, and the preparation of drinking water aboard a ship at sea all involve the measurement of specific gravity. Needless to say, a quick, facile method for determining this solution property would greatly enhance the state of these technologies, as well as any others where rapid, accurate determination of specific gravity would be beneficial. Thus, for example, if a medical laboratory technician could accurately measure the specific gravity of a urine sample in a matter of seconds, not only would such rapid results aid the physician in diagnosis, but also laboratory efficiency would increase manyfold.

Although the present invention lends itself to a vast range of applications, for purposes of clarity this discussion will be couched largely in terms of the determination of the ionic strength or specific gravity of urine. Applications to other disciplines will become apparent from an understanding of how this invention relates to urinalysis.

The determination of urine specific gravity is of considerable value in the understanding and clinical management of electrolyte disturbances. Hence, complete urinalysis should, and usually does, include a specific gravity determination. Generally, such a determination would include the measurement of specific gravity directly with a suitable device, but equally useful is the measurement of some related property, such as osmolality or ionic strength, which can then be referred back to corresponding specific gravity values.

1.2 Relationship Between Specific Gravity and Ionic Strength

Specific gravity is a dimensionless term and relates, in the case of a solution, to the ratio of the weight of a certain volume of the solution at a given temperature, to that of an equal volume of water, also at some specified temperature. For solutions such as urine, the specific gravity is a function of the number, density, ionic charge, and weight of the various species of dissolved solutes.

The term "ionic strength" refers to the mathematical relationship between the number of different kinds of ionic species in a particular solution and their respective charges. Thus, ionic strength $\mu$ is represented mathematically by the formula $$\mu = \tfrac{1}{2} \sum_i c_i z_i^2 \qquad (1)$$

in which c is the molar concentration of a particular ionic species and z the absolute value of its charge. The sum $\Sigma$ is taken over all the different kinds of ions in solution.

The relationship between ionic strength and specific gravity has a definable mathematical correlation. In the case of dilute NaCl, for example, in which the solution has a molal concentration of c, equation (1) reduces to $$\mu = \tfrac{1}{2} \sum_i c_i z_i^2 \qquad (1)$$

$$= \tfrac{1}{2} [(c_{Na^+})(1) + (c_{Cl^-})(1)] \qquad (2)$$

$$\mu = c \qquad (3)$$

Moreover, it is known that the relationship between molality c and molarity M of a given solution is $$c = M/\rho \qquad (4)$$

where $\rho$ is the density of the solvent. Substituting c from equation (3) into equation (4) yields the relationship between ionic strength and molarity.

$$\mu = M/\rho \qquad (5)$$

For dilute NaCl, it has been found experimentally that the following relationships between molar concentration (M) and specific gravity (SG) exist:

| SG | ΔSG | M NaCl | ΔM |
|---|---|---|---|
| 1.005 | 0.120 | | |
| | | 0.240 | 0.120 |
| 1.010 | 0.005 | | |
| | | 0.360 | 0.120 |
| 1.015 | 0.005 | | |
| | | 0.488 | 0.128 |
| 1.020 | 0.005 | | |
| | | 0.613 | 0.125 |
| 1.025 | 0.005 | | |

The data shows that for every incremental increase of 0.12M in NaCl concentration, a corresponding change in SG of 0.005 occurs. Using this relationship, SG can be defined mathematically as $$SG = 1 + \frac{0.005M}{0.12} \quad (6)$$

Substituting (5) into (6) we have $$SG = 1 + \frac{0.005\mu\rho}{0.12} \quad (7)$$

Where the solvent is water, $\rho = 1$ and equation (7) reduces to $$SG = 1 + \frac{0.005\mu}{0.12} \quad (8)$$

2. BACKGROUND OF THE INVENTION

Prior to the present invention, most methods for determining specific gravity utilized hydrometers, urinometers, pycnometers, gravimeters and the like. Although these prior art procedures are satisfactorily sensitive in most cases, they involve fragile, bulky instruments which must be constantly cleaned, maintained, and calibrated in order to continuously assure their reliability. In addition, there are many inconveniences associated with the mechanics of using these instruments. There may be a difficulty in reading the miniscus. Froth or bubbles on the liquid surface may interfere with the reading. There is a tendency for urinometers to adhere to the sides of the vessel containing the liquid sample. In the case of urine, the sample quantity is frequently inadequate for accommodating one of the aforementioned devices.

A recent breakthrough in which all of the above disadvantages have been virtually eliminated, and which affords rapid osmolality (ergo, specific gravity) determination, is disclosed in U.S. Pat. No. 4,015,462, issued to Greyson, et al., and assigned to the present assignee. This patent describes an invention in which a carrier matrix is incorporated with osmotically fragile microcapsules, the walls of which are composed of a semi-permeable membrane material. Encapsulated inside the walls is a solution containing a coloring substance. When the capsules come in contact with a solution having a lower osmolality than that within the capsules, an osmotic gradient occurs across the capsule walls in the direction of the lower osmolality, thereby increasing the hydrostatic pressure within the capsules, thus causing them to swell and, ultimately, to rupture, releasing their colored contents. The amount of color formed from this phenomenon is a function of the specific gravity of the solution.

Thus, it is seen that, besides the numerous devices which measure specific gravity directly, it is also possible to measure specific gravity using an indirect means such as the osmolality of a solution.

Yet another way of estimating specific gravity without measuring it directly involves a determination which is proportional to the ionic strength of a solution, the correlation of which parameters has already been discussed in section 1.1, supra. Such an approach is utilized in U.S. Pat. No. 4,318,709 issued to Falb, et al., and assigned to the present assignee. Since it is well known that the specific gravity of an aqueous system is greatly affected by the presence of charged species, it is possible to closely approximate the specific gravity of the respective solutions via measurements proportional to their ionic strengths, and refer those measurements to a precalibrated reference system. The Falb, et al., patent makes use of such a relationship.

The Falb et al. patent discloses the use of weakly acidic or basic polyelectrolytes which have been at least 50% neutralyzed with a base (such as NaOH) or an acid (such as HCl), respectively. Depending on the ionic strength of the test solution, an intramolecular pH change may occur in the polymer, the degree of which is a barometer of ionic strength. A pH indicator such as a pH meter or pH-sensitive compound reflects the pH change (or lack thereof) instigated by the sample ionic strength.

Both the osmolality approach and the ionic strength approach to indirectly determining specific gravity could conceivably be affected insofar as accuracy is concerned by the presence of nonionic species. However, it has been found that such nonionic constituents as glucose, protein and urea do not effectively lead to anomalous or substantially inaccurate results with the Falb, et al. test except at very high concentrations. See Burkhardt, et. al., *Clinical Chemistry*, 28, 2068–2072 (1982).

U.S. Pat. No. 4,108,727 is directed to a method for removing this potential source of inaccuracy, and discloses a device in which the specific gravity-sensitive system contains an ionizing agent capable of converting the nonionic solute to ionized species.

U.S. Pat. No. 3,449,080 discusses measuring dissolved sodium or chloride ions. This reference is directed to a test device for determining the concentrations of these ions in body sweat. There is disclosed in this patent the use of ion exchange resins together with a pH indicator. Using this device, the presence of sodium or chloride ions is said to be determined through a color change in the ion exchange resin caused by the pH indicator. Whereas this reference purports to disclose a way of measuring ionic strength, it was found by the present inventors that such teachings, as set forth in the examples, were inapplicable to the measurement of specific gravity.

To summarize the present background of specific gravity measurement prior to the present invention, many methods are known for assaying that solution parameter, both direct and indirect. Direct measurement includes utilizing devices which are fragile, bulky and expensive, and which must be constantly cleaned, maintained and calibrated. Of the indirect methods, the measurement of the colligative solution property known as osmolality can provide an accurate correlation to specific gravity. In addition, the relationship between specific gravity and the ionic strength of a solution can be employed, by utilizing partially neutralized polyelectrolytes and a pH indicator. Weak polyelectrolytes are said to be useful in gauging the concentration of sodium and/or chloride ions in body sweat.

The present invention provides a departure from the prior art which enables dramatic improvements in the measurement of ionic strength, ergo specific gravity. Practice of the invention affords greater sensitivity in differentiating various specific gravity levels, as well as enhanced resistance to interference from test sample-to-test sample pH variations.

3. SUMMARY OF THE INVENTION

Briefly, the present invention relates to a test means, device, and method for determining the specific gravity of an aqueous test sample. The test means comprises a weakly acidic polyelectrolyte salt, that is, a weakly acidic polyelectrolyte polymer which has been at least partially neutralized with a specific quaternary ammonium salt or base; and an indicator substance capable of producing a detectable response to ion exchange between the polyelectrolyte and the test sample. The device of the present invention comprises a carrier matrix incorporated with the test means. The method of the present invention comprises contacting a test sample with the device or test means and observing a detectable response such as a change in color, pH or enzyme activity.

The weakly acidic polyelectrolyte polymer is at least about 50 percent neutralized. Thus, at least about 50 percent of the carboxyl groups attached to the polymer backbone are present in the form of the salt of a quaternary ammonium ion. From a generic standpoint, such a polyelectrolyte salt can be thought of as having the structure

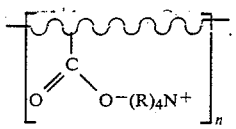

in which the wavy line represents any polymeric backbone, which may be substituted with moieties in addition to and other than, the specified carboxyl groups, and in which n represents the number of repeating units in the polymer chain. The R substituents of the ion $(R)_4N^+$ can be, same or different, hydrogen, lower alkyl, or aryl. At least one of the R groups is other than hydrogen.

4. BRIEF DESCRIPTION OF THE DRAWINGS

In order to further illustrate the present invention and its advantages, the attached drawings have been provided.

FIG. I presents performance data from tests comparing the present invention with the prior art. It graphically portrays the surface pH developed in a pH-sensitive filter paper, one comprising the polyelectrolyte salt claimed herein, the other a prior art specific gravity-sensitive system.

FIG. II presents similar data in yet another fashion. This graph shows the change in pH ($\Delta pH$) caused by various specific gravity increments.

5. DEFINITIONS

Certain terms used in the present discussion should at this point be mentioned to assure that the reader is of the same mind as the author as to their respective meanings. Thus the following definitions are provided in order that the reader be fully apprised of the scope of the present invention, and that he be fully enabled to formulate and use it.

1. The term "lower alkyl" includes alkyl groups having one to six carbon atoms. Thus, it includes methyl, ethyl, n-propyl, isopropyl, n-butyl, isobutyl, tert-butyl and all of the pentyl and hexyl isomers. Such groups may be substituted or unsubstituted although, of course, substituents which would adversely affect the use of the invention by being reactive so as to interfere with the intended functions of its components are clearly outside the intended meaning of the term. Such interfering substituents are easily determinable at the laboratory bench through routine experimentation in keeping with the teachings of the present disclosure and the Examples.

2. As used herein, the term "aryl" relates to groups having one or more six-membered ring systems which contain the structure of benzene or other aromatic derivatives. Typical of aryl groups are phenyl ($C_6H_5$—), benzyl ($C_6H_5CH_2$—), and naphthyl. Like the lower alkyl groups, the aryl groups may be substituted or unsubstituted, provided the substituent not interfere with the intended function of the invention, i.e., the measurement of ionic strength or specific gravity.

3. As used herein, the term "quaternary ammonium salt" connotes a departure from ordinary usage of these words. In the present disclosure a quaternary ammonium salt is intended to mean a salt having the formula $(R)_4N^+X^-$ in which one or more of the R substituents is hydrogen, lower alkyl or aryl, and X is halogen, in which at least one of R is other than hydrogen.

4. Likewise, "quaternary ammonium hydroxide" is intended to mean a compound of the formula $(R)_4N^+OH^-$ in which at least one of the R substituents is lower alkyl or aryl.

5. "Quaternary ammonium ion" is intended to mean the positively charged ionic constituent of a quaternary ammonium salt or hydroxide. It is an ion of the formula $(R)_4N^+$ where at leaast one R substituent is lower alkyl or aryl.

6. "Polyelectrolyte salt" is intended to mean a weakly acidic polyelectrolyte polymer, at least about 50 percent of the carboxyl groups of which have been chemically combined with a quaternary ammonium ion. The salt is one in which the carboxyl proton ($H^+$) has been replaced by the quaternary ammonium ion.

6. POLYELECTROLYTES AND THEIR SALTS

6.1 Weakly Acidic Polyelectrolytes

The presently claimed test means comprises, as one ingredient, a weakly acidic polyelectrolyte. Numerous examples of such polymers are known in the art, their common characteristics centering about the presence of acidic pendant groups which only partially dissociate when the polymer is subjected to an aqueous environment. Most polyelectrolytes are soluble or partially soluble in water, and are readily ionizable, depending on the ionic nature of (a) the aqueous system and (b) the ionizable species on the polymer chain.

Thus a polyelectrolyte is branded weakly or strongly acidic depending on its ionic behavior in solution. Generally, a polyelectrolyte which nearly completely ionizes when contacted with water, such as poly(vinylsulfonic acid) and poly(styrene sulfonic acid), are considered strong polyelectrolytes. Weakly acidic polyelectrolytes on the other hand, contain weakly acidic ionizable groups, such as carboxyl group. The charge density along the molecular chain of these polymers can be varied by varying the degree of substitution, as well as the degree of neutralization. Examples of weakly acidic polyelectrolytes which find particular applicability to the present invention are poly(acrylic acid), poly(maleic acid), maleic acid/methylvinyl ether copolymer, poly(methacrylic acid), and styrene/maleic acid copolymer. Especially suitable is a polymer known as Gantrez®AN-119, a maleic anhydride/methylvinyl ether copolymer marketed by General Aniline and Film Corporation.

While the composition and test means of the present invention includes weakly acidic polyelectrolytes, at least some of the functional groups of the polymer (e.g., COOH) are first partially reacted to form a salt, as specified supra. Thus, the polyelectrolyte salt can be prepared by titrating the polymer with a quaternary ammonium hydroxide until at least about 50% of the carboxyl groups have been neutralized.

6.2 Quaternary Ammonium Ions

The quaternary ammonium ion which is included in the present invention can be obtained through well-established syntheses. Quaternary ammonium salts can be formed through reaction of alkyl or aryl halides with tertiary amines. For the purposes of the present invention, such compounds include one or more substituent groups, the remaining N-substituents being hydrogen. These salts are ionic substances and, in aqueous solution, are capable of replacing the proton (H$^+$) of a carboxyl group, thus forming a salt such as the polymer salts included in the present invention. Formation of quaternary ammonium salts is exemplified by the equation

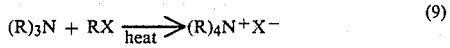

$$(R)_3N + RX \xrightarrow{heat} (R)_4N^+X^- \qquad (9)$$

in which R is as defined, supra, and X is a halogen.

Preparation of the weakly acidic polyelectrolyte salts can ideally be performed through the use of quaternary ammonium hydroxide having the formula $(R)_4N^+OH^-$ in which R is as defined, supra. These compounds can be prepared from quaternary ammonium salts by reaction with an alkali in accordance with

$$(R)_4N^+X^- + MOH \rightleftharpoons (R)_4N^+OH^- + MX \qquad (10)$$

in which X is halogen and M is an alkali metal.

An alternative method of preparation of the quaternary ammonium hydroxide is through treatment of the corresponding ammonium halide in aqueous solution with silver hydroxide in accordance with

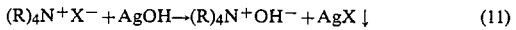

$$(R)_4N^+X^- + AgOH \rightarrow (R)_4N^+OH^- + AgX\downarrow \qquad (11)$$

This procedure overcomes the problem of the equilibrium in (10), because of the insolubility of silver halide. Thus, if the equilibrium is shifted to the right the desired hydroxide product can then be isolated by filtering the aqueous solution followed by evaporation. The organic base can be obtained as a crystalline solid, usually a deliquescent hydrate.

Exemplary of quaternary ammonium hydroxides which produce salts with polyelectrolytes useful in the present invention are tetramethyl, tetraethyl, tetrabutyl, tributylmethyl, trimethylbutyl, trimethylphenyl, trimethylbenzyl, trimethyl-2-hydroxyethyl, trimethyl, triethyl, and tributyl ammonium hydroxides.

6.3 Preparation of the Polyelectrolyte Salt

The weakly acidic polyelectrolyte salt of the present invention may be prepared by aqueous titration of the polyelectrolyte polymer using a solution of a quaternary ammonium hydroxide. The carboxyl groups are preferably at least about 50 percent neutralized. An ideal neutralization range, and that presently found most preferred in the present invention, is from about 65 to about 95% neutralization, 90% having thus far been found to be optimum in providing the largest separation in pH change or other detectable response with respect to specific gravity or ionic strength.

7. pH INDICATORS MEANS

Another element of the present invention is an indicator means. It can take on such diverse forms as a pH indicator compound, an enzymatic system whose enzyme/substrate function is responsive to subtle pH changes, a pH meter, and a pH-sensitive antigen/antibody system. Thus, known pH-sensitive chromogenic reagent compounds can be employed, and these can provide a change in or appearance of color, observable by the person performing the measurement, which is indicative of the ionic strength or specific gravity of the system being tested. If a chromogen is used, a reference color system can be established beforehand, so that a quick visual comparison of the composition and the reference system provides the sought-after results. Examples of chromogens suitable for use in the present invention are bromothymol blue, alizarin, bromcresol purple, phenol red and neutral red; bromothymol blue having been found to be especially suitable.

Alternatively, the indicator means can take the form of a pH meter, whereby small changes in pH ($\Delta$pH) can be monitored directly, without resorting to visual observation of color change. One particularly suitable approach is to use the pH meter in conjunction with a surface pH electrode. The pH meter response can then be observed over various ionic strength values and a reference system can be established, a particular change in pH corresponding to a particular test sample ionic strength.

Yet another ramification of the indicator means is a pH-sensitive enzyme-based system, whereby subtle changes in pH caused by the polyelectrolyte/ionic strength interaction can trigger the onset of enzymatic activity, or which can change kinetic reaction parameters such as the $K_M$ for a particular enzymatic reaction. Thus an enzymatic system capable of providing a detectable response can be triggered to produce that response in accordance with the specific gravity or ionic strength of a test sample. For example, the enzyme chymotrypsin is known to be sensitive to pH in acting on the substrate p-nitrophenyl acetate to yield the yellow product, p-nitrophenol. The reaction rate dramatically increases from pH 6 to 8 and the appearance of p-nitrophenol is markedly enhanced by pH increases in that range.

Similarly, an antigen-labeled substrate can be employed. The pH dependence of antigen/antibody reactions is well known, and the indicator means of the present invention can include such a labeled substrate and the antibody for the label. Change in pH can be measured by change in substrate available for a corresponding enzymatic reaction.

8. THE TEST DEVICE

The test device of the present invention comprises a suitable carrier matrix which has been incorporated with a polyelectrolyte salt and an indicator compound or other pH-sensitive means, together with other inert ingredients. In an especially convenient format, a portion of the composition-bearing matrix can be mounted on one end of a plastic strip, the other end serving as a handle. Such a device can then be used to assay the ionic strength or specific gravity of a test sample merely by dipping the matrix into the sample, removing it, and observing the color of the matrix, e.g., by comparing it to a reference color chart.

8.1 The Carrier Matrix

The carrier matrix is usually, but not necessarily, a porous substance such as filter paper. Other art-recognized forms of carrier matrix materials are felt, porous ceramic strips, and woven or matted glass fibers (U.S. Pat. No. 3,846,247). Also suggested are the use of wood, cloth, sponge material and argillaceous substances (U.S. Pat. No. 3,552,928). All such carrier matrix materials are feasible for use in the present invention, as are others. It has been found that filter paper is especially suitable.

8.2 Incorporation of the Composition With The Matrix

The method by which reagent composition of the present invention is incorporated with a carrier matrix is intended as broad in scope, and depends largely on the nature of the matrix. For example, where the carrier is a polymeric film, the polyelectrolyte salt and pH indicator can be cast as a film by combination in solution either alone or with a suitable binder, Followed by application with a doctor blade. Alternatively, the composition can be homogeneously blended with the film polymer, such as by forming a solution of both polymer and composition; or on the composition can be blended with melted polymer. The homogeneous blend can then be used as a film (if the solution approach is adopted), or melted into a film, such as by use of heated platens. Many carrier matrices lend themselves to reagent application using spraying and printing techniques, such as ink jet printing.

In a preferred embodiment, filter paper is wetted with a solution or suspension of the polyelectrolyte salt in water or other convenient excipient and then dried. The polyelectrolyte-bearing filter paper is subsequently incorporated with the desired indicator means. Typically, the paper is wetted with a solution of a pH-sensitive chromogenic indicator (such as bromothymol blue) in methanol or other suitable solvent such as ethanol, N,N-dimethylformamide, or dimethylsulfoxide, and subsequently dried. Alternatively, a one-dip method can be used whereby the polyelectrolyte and indicator means are simultaneously present in the initial solution or suspension.

8.3 Preparation of a Dip-and-Read Device

As indicated above, the reagent-bearing carrier matrix can be mounted on a backing material if desired. The test device, in a preferred embodiment, thus comprises a filter paper carrier matrix incorporated with a polyelectrolyte salt and indicator means, the matrix being affixed to one end of an elongated piece of transparent polystyrene film, the other end serving as a handle. The matrix is secured to the film by any suitable means, for example by using double-faced adhesive tape (Double Stick ® available from 3M Company). In use, such a device is held by the free end of the polystyrene film backing material and the matrix end is immersed into the test sample (e.g., urine) and quickly removed. Any color formation or other detectable response is observed after a predetermined time and compared with a color reference standard corresponding to responses to known solution ionic strengths or specific gravities.

9. REFERENCE STANDARD

The particular reference standard employed depends on whether the test means is used by itself or incorporated with a carrier matrix, and depends as well on the particular indicator means employed. Thus, if the polyelectrolyte salt is added directly to the test sample and the indicator means is a pH meter, a reference standard can be devised by adding a standard weight of polyelectrolyte salt to a standard volume of a solution of known ionic strength. The pH before and after polyelectrolyte salt addition is recorded using the pH meter. This procedure is followed for a series of solutions having differing known ionic strengths. To determine the ionic strength of an unknown test sample, the same procedure is followed and the pH change compared with those of the known solutions.

Where a test device comprising a carrier matrix containing polyelectrolyte salt and a colorometric pH indicator is employed, a reference standard can comprise a series of color blocks depicting the color developed by the carrier matrix after a predetermined time in response to solutions of known ionic strengths. When testing an unknown sample, the carrier matrix of a test device is immersed in the sample, removed, and observed for the appearance of or change in color after the predetermined time. The carrier matrix is at that time compared with the reference standard color blocks to ascertain the ionic strength or specific gravity of the sample.

10. EXAMPLES

The following Examples are provided to further assist the reader in making and using the present invention. Thus, preferred embodiments are described and analyzed. The Examples are meant to be illustrative only, and are in no way intended as limiting the scope of the invention described and claimed hereto.

10.1 Preparation of Polyelectrolyte Salts

A series of experiments was conducted to prepare salts of various weakly acidic polyelectrolytes and quaternary ammonium hydroxides. The polyelectrolytes employed were maleic acid/vinylmethyl ether copolymer (Gantrez AN-119 obtained from GAF Corporation), and maleic acid/ethylene copolymer (PMAET). The quaternary ammonium hydroxides used were tetramethyl ammonium hydroxide, tetrabutyl ammonium hydroxide, tetraethyl ammonium hydroxide, tributylmethyl ammonium hydroxide, trimethyl-2-hydroxyethyl ammonium hydroxide, and benzyltrimethyl ammonium hydroxide.

A standard solution of the particular polyelectrolyte polymer to be studied as prepared, and for each experiment two aliquots were employed. To one was added a measured amount of sodium chloride. The other comprised a solution of the polyelectrolyte in distilled water. To each aliquot was added a predetermined amount of a particular quaternary ammonium hydroxide sufficient to effect 75% substitution of the polyelectrolyte carboxyl groups. In calculating the amount of hydroxide to add, it was assumed that each of the polymers comprised alternating groups of the respective comonomers.

For each of the above-mentioned polyelectrolyte polymers, a set of solutions of 25 milliliters (ml) each was prepared in distilled water. The first solution contained sufficient copolymer to yield 0.015 moles per liter of carboxyl groups. To one of the solutions was added sufficient sodium chloride to make the solution 1.1M NaCl. To each of the solutions was added a quantity of the respective quaternary ammonium hydroxide to correspond to 0.0113 moles per liter of the corresponding quaternary ammonium ion. The exact concentrations and amounts are listed in Table I.

specific gravity of aqueous solutions containing varying concentrations of sodium chloride.

TABLE I

| Polyelectrolyte Solution | | Quaternary Ammonium Hydroxide | | % Polyelectrolyte Neutralization |
|---|---|---|---|---|
| Type | Amount | Type | Amount | |
| Gantrez AN 119 | 25 ml at 2.34 g/dl in water | Tetramethyl ammonium hydroxide.5H$_2$O | 1.013 g | 75 |
| Gantrez AN 119 | 25 ml at 2.34 g/dl in water | Tetrabutyl ammonium hydroxide (40 g/dl in water) | 3.66 ml | 75 |
| Gantrez AN 119 | 25 ml at 2.34 g/dl in water | Tetraethyl ammonium hydroxide (20 g/dl in water) | 4.14 ml | 75 |
| Gantrez AN 119 | 25 ml at 2.34 g/dl in water | Tributylmethyl ammonium hydroxide (40 g/dl in water) | 3.06 ml | 75 |
| Gantrez AN 119 | 25 ml at 2.34 g/dl in water | 2-hydroxyethyltrimethyl ammonium hydroxide (50 g/dl in water) | 1.37 ml | 75 |
| Gantrez AN 119 | 25 ml at 2.34 g/dl in water | Benzyltrimethyl ammonium hydroxide (40 g/dl in water) | 2.36 ml | 75 |
| PMAET | 25 ml of 2 g/dl in water | Tetramethyl ammonium hydroxide (28.6 g/dl in water) | 3.75 ml | 75 |
| PMAET | 25 ml of 2 g/dl in water | Tetrabutyl ammonium hydroxide (40 g/dl in water) | 3.83 ml | 75 |

10.2 Preparation of the Test Device

A test device sensitive to ionic strength or specific gravity was prepared by incorporating into filter paper a solution containing Gantrez AN-119 which had been titrated with a quaternary ammonium hydroxide, and the pH indicator bromothymol blue.

Into a beaker was placed 100 milliliters of a solution of 2.34 grams per deciliter (g/dl) of Gantrez AN-119 and 0.1 grams per deciliter of bromothymol blue. This solution was titrated to a pH of 9.5±0.02 with tetramethyl ammonium hydroxide.

A piece of Eaton & Dikeman No. 204 filter paper was dipped into the solution, removed and dried in a air oven at about 50° C. Squares of the impregnated dried filter paper were mounted at the end of small rectangular strips of polystyrene film measuring about 25 millimeters by about 4 inches. Thus, the polystyrene film strip had a 25 millimeter square of impregnated paper mounted at one end, the other end serving as a convenient handle. The filter paper squares were mounted using double-faced adhesive tape (Double-Stick ® obtained from 3M Company).

Test devices were similarly prepared using Gantrez AN-119 and tributylmethyl ammonium hydroxide. A solution was prepared comprising 29.3 milliliters of an aqueous solution of Gantrez AN-119 having a concentration of 4 grams of polymer per 100 milliliters. To this was added 7.2 milliliters of an aqueous solution of tributylmethyl ammonium hydroxide at a concentration of 40 grams per 100 milliliters. To this mixture was added 0.05 grams (g) of bromothymol blue and 0.016 grams methyl red. The mixture was then diluted with distilled water to a final volume of 50 milliliters. The pH of this solution was measured to be 10.30 (10.26 after standing for one hour).

The solution was then used to impregnate a piece of Eaton & Dikeman filter paper as above. The filter paper was similarly dried and mounted on a piece of polystyrene film.

The test devices prepared in these experiments were found to be useful in measuring the ionic strength or specific gravity of aqueous solutions containing varying concentrations of sodium chloride.

10.3 Evaluation of the Test Device

A series of experiments was conducted in order to determine the efficacy of the test device of the present invention in determining specific gravity. The device was compared to a presently commercially available test device prepared in conformity with the claims of U.S. Pat. No. 4,318,709, Falb, et al. The data from these experiments can be found in FIG. I.

The devices of the present invention which were used in this experiment were prepared as described in section 10.2, supra. Instead of mounting the impregnated dried filter paper onto polystyrene strips, however, squares measuring 1 centimeter on a side were cut from the impregnated filter paper and used for the present evaluation.

In order to provide a comparison with the present invention, a test device was prepared which corresponded to the presently commercially available specific gravity measuring area of N-MULTISTIX-SG, a multiple analyte test device marketed by the Ames Division of Miles Laboratories, Inc. This impregnated filter paper was prepared from a solution containing 23.4 grams of Gantrez AN-119 per liter of deionized water, and 1.2 grams of bromothymol blue per liter. An aliquot of this solution was titrated with NaOH until the resultant solution pH was 7.75 as measured with a standard pH electrode and an Orion Model 701 digital pH meter. A strip of filter paper (Eaton & Dikeman No. 204) was immersed in the partially titrated aliquot and subsequently dried. After drying, the filter paper was mounted on a polystyrene film using double-faced adhesive tape (Double-Stick obtained from 3M Company). The resultant test devices each comprised a strip of polystyrene film at one end of which was mounted a 1 centimeter square of the impregnated filter paper.

In order to compare the present invention with the NaOH-titrated Gantrez, a series of sodium chloride solutions was prepared each having a known concentration of sodium chloride. Each of the test devices was dipped in one of the sodium chloride solutions and the surface pH of the impregnated filter paper was measured using a flat-surface Polymer-body Combination Electrode 13-639-83 obtained from Fisher Scientific Company. The pH value was recorded 60 seconds after removal of the strip from a sample solution. The concentrations and specific gravities of the sodium chloride solutions, as well as the surface pH of the respective devices following dipping into the sodium chloride solutions are recorded in Table II.

TABLE II

| NaCl Solution | | Surface pH of Test Device | | ΔpH Between Specific Gravity Levels | |
|---|---|---|---|---|---|
| Sp. Gr. | Conc. (M) | Prior Device | Present Invention | Prior Device | Present Invention |
| 1.000 | 0.000 | 7.78 | 9.21 | 0.62 | 1.12 |
| 1.005 | 0.120 | 7.16 | 8.09 | 0.18 | 0.32 |
| 1.010 | 0.241 | 6.98 | 7.77 | 0.11 | 0.20 |
| 1.015 | 0.364 | 6.87 | 7.57 | 0.09 | 0.21 |
| 1.020 | 0.488 | 6.78 | 7.36 | 0.10 | 0.21 |
| 1.025 | 0.613 | 6.68 | 7.15 | 0.07 | 0.14 |
| 1.030 | 0.737 | 6.61 | 7.01 | | |

This data is plotted graphically in FIG. I and shows that with the present invention a marked departure in the change in pH with respect to specific gravity occurs, whereas similar changes with the prior art device were not nearly as pronounced.

Yet another useful tool for comparison is the relative change in pH between varying specific gravity levels (ΔpH). Since the pH indicator response (or color change) is at least approximately proportional to ΔpH, it is clear that the greater the pH change for a particular device from one specific gravity level to another, the greater the color change will be, and the more the accuracy of the test will be enhanced.

ΔpH data from Table II has been plotted in FIG. II to provide a comparison of the present invention with prior art device as prepared above (i.e., the specific gravity test area of N-MULTISTIX-SG). FIG. II shows that the present invention affords from 78% to 133% greater ΔpH with the present invention, thereby affording a dramatic increase in color response over the state-of-the-art device prior to the present invention.

What is claimed is:

1. In a test means for determining the ionic strength or specific gravity of an aqueous test sample, wherein said test means comprises a weakly acidic polyelectrolyte polymer, and an indicator means capable of producing a detectable response to ion exchange between said polyelectrolyte and said sample;

the improvement wherein at least 50 percent of the acidic groups of said polyelectrolyte are present in the form of the salt of an ion having the structure

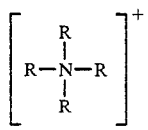

in which the R substituents, same or different, are hydrogen, lower alkyl or aryl, with the proviso that at least one of R be other than hydrogen.

2. The improved test means of claim 1 in which the polyelectrolyte is poly(acrylic acid), poly(maleic acid), maleic acid-vinylmethyl ether copolymer, poly(methacrylic acid), or styrene-maleic acid copolymer.

3. The improved test means of claim 1 in which the polyelectrolyte is maleic acid-vinylmethyl ether copolymer.

4. The improved test means of any one of claims 1–3 in which the R substituents, same or different, are hydrogen, methyl, ethyl, propyl, butyl, phenyl, benzyl, or 2-hydroxyethyl.

5. The improved test means of any one of claims 1–3 in which the ion is tributylmethyl ammonium.

6. The improved test means of any one of claims 1–3 in which the ion is tetrabutylammonium.

7. The improved test means of claim 1 in which said indicator means is a pH indicator substance.

8. The improved test means of claim 1 in which said indicator means is bromothymol blue.

9. The improved test means of claim 1 in which the polyelectrolyte is maleic acid-vinyl ether copolymer; the ion is tetramethyl ammonium, tetraethyl ammonium, tetrabutyl ammonium, tetrapropyl ammonium, tributylmethyl ammonium, phenyltrimethyl ammonium, benzyltrimethyl ammonium or 2-hydroxyethyltrimethyl ammonium; and the indicator means is a pH indicator substance.

10. The improved test means of claim 9 in which the ion is tributylmethyl ammonium.

11. The improved test means of claim 9 in which the indicator means is bromothymol blue.

12. The improved test means of any one of claims 9–11 in which about 75 to 94 percent of the acidic groups of the polyelectrolyte are in the form of a salt of said ion.

13. A test device for determining the ionic strength or specific gravity of an aqueous test sample, the device comprising a carrier matrix incorporated with the test means of any one of claims 1–3.

14. A test device for determining the ionic strength or specific gravity of an aqueous test sample, the device comprising a carrier matrix incorporated with the test means of claim 4.

15. A test device for determining the ionic strength or specific gravity of an aqueous test sample, the device comprising a carrier matrix incorporated with the test means of claim 5.

16. A test device for determining the ionic strength or specific gravity of an aqueous test sample, the device comprising a carrier matrix incorporated with the test means of claim 7.

17. A test device for determining the ionic strength or specific gravity of an aqueous test sample, the device comprising a carrier matrix incorporated with the test means of claim 8.

18. A test device for determining the ionic strength of specific gravity of an aqueous test sample, the device comprising a carrier matrix incorporated with the test means of any one of claims 9–11.

19. A method for determining the ionic strength or specific gravity of an aqueous test sample, the method comprising contacting the sample with the test means of any one of claims 1-3, and observing a detectable response.

20. A method for determining the ionic strength or specific gravity of an aqueous test sample, the method comprising contacting the sample with the test means of claim 4, and observing a detectable response.

21. A method for determining the ionic strength or specific gravity of an aqueous test sample, the method comprising contacting the sample with the test means of claim 5, and observing a detectable response.

22. A method for determining the ionic strength or specific gravity of an aqueous test sample, the method comprising contacting the sample with the test means of claim 7, and observing a detectable response.

23. A method for determining the ionic strength or specific gravity of an aqueous test sample, the method comprising contacting the sample with the test means of claim 8, and observing a detectable response.

24. A method for determining the ionic strength or specific gravity of an aqueous test sample, the method comprising contacting the sample with the test means of any one of claims 9-11, and observing a detectable response.

25. A method for determining the ionic strength or specific gravity of an aqueous test sample, the method comprising contacting the sample with the test device of claim 13, and observing a detectable response.

26. A method for determining the ionic strength or specific gravity of an aqueous test sample, the method comprising contacting the sample with the test device of claim 14, and observing a detectable response.

27. A method for determining the ionic strength or specific gravity of an aqueous test sample, the method comprising contacting the sample with the test device of claim 15, and observing a detectable response.

28. A method for determining the ionic strength or specific gravity of an aqueous test sample, the method comprising contacting the sample with the test device of claim 16, and observing a detectable response.

29. A method for determining the ionic strength or specific gravity of an aqueous test sample, the method comprising contacting the sample with the test device of claim 17, and observing a detectable response.

30. A method for determining the ionic strength or specific gravity of an aqueous test sample, the method comprising contacting the sample with the test device of claim 18, and observing a detectable response.

31. A method for preparing a test device for determining the ionic strength or specific gravity of an aqueous test sample, the method comprising the steps of reacting a weakly acidic polyelectrolyte polymer with sufficient quaternary ammonium hydroxide to form a salt of at least 50 percent of the acidic groups of the polyelectrolyte, thereby forming a polyelectrolyte salt, and incorporating a carrier matrix with the polyelectrolyte salt and a pH indicator.

32. The method of claim 31 wherein sufficient quaternary ammonium hydroxide is used to form a salt of about 75 to 95 percent of the acidic groups of the polyelectrolyte.

33. The method of claim 31 or 32 in which the carrier matrix is contacted with a solution or suspension of the polyelectrolyte salt and pH indicator in a suitable solvent, and dried.

34. A method for preparing a test device for determining the ionic strength or specific gravity of an aqueous test sample, said method comprising the steps of preparing an aqueous solution of a maleic acid-methylvinylether copolymer, adding an aqueous solution of a quaternary ammonium hydroxide having the structure

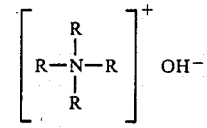

in which the R substituents, same or different, are hydrogen, lower alkyl or aryl, with the proviso that at least one of R be other than hydrogen, said solution being added in an amount sufficient to react with at least 50 percent of the carboxyl groups of said copolymer, thereby forming a polyelectrolyte salt solution, contacting a carrier matrix with the polyelectrolyte salt solution thereby incorporating the salt with the matrix, drying the polyelectrolyte salt-incorporated matrix, and incorporating a pH indicator with said dried matrix.

35. The method of claim 34 wherein the pH indicator is bromothymol blue and the indicator is incorporated with the dried polyelectrolyte salt-incorporated matrix by preparing a solution of said indicator in methanol, and contacting the matrix with the indicator solution.

* * * * *